United States Patent [19]

Lew et al.

[11] Patent Number: 5,162,043

[45] Date of Patent: * Nov. 10, 1992

[54] IONTOPHORETIC DELIVERY DEVICE

[75] Inventors: Patrick J. Lew, Mountain View; J. Richard Gyory, San Jose, both of Calif.

[73] Assignee: Alza Corporation, Palo Alto, Calif.

[ * ] Notice: The portion of the term of this patent subsequent to Jan. 28, 2009 has been disclaimed.

[21] Appl. No.: 788,661

[22] Filed: Nov. 6, 1991

Related U.S. Application Data

[63] Continuation of Ser. No. 502,608, Mar. 30, 1990, Pat. No. 5,084,006.

[51] Int. Cl.⁵ .............................................. A61N 1/30
[52] U.S. Cl. ...................................... 604/20; 128/802
[58] Field of Search ................. 604/20; 128/639-641, 128/798, 802, 803

[56] References Cited

U.S. PATENT DOCUMENTS

| | | | |
|---|---|---|---|
| 3,991,755 | 11/1976 | Vernon et al. | 604/20 |
| 4,141,359 | 2/1979 | Jacobsen et al. | 604/20 |
| 4,144,317 | 3/1979 | Higuchi et al. | 424/21 |
| 4,250,878 | 2/1981 | Jacobsen et al. | 604/20 |
| 4,383,529 | 5/1983 | Webster | 604/20 |
| 4,398,545 | 8/1983 | Wilson | 128/798 |
| 4,474,570 | 10/1984 | Ariura et al. | 604/20 |
| 4,619,252 | 10/1986 | Ibbott | 604/20 |
| 4,702,732 | 10/1987 | Powers et al. | 604/20 |
| 4,731,049 | 3/1988 | Parsi | 604/20 |
| 4,764,164 | 8/1988 | Sasaki | 604/20 |
| 4,767,401 | 8/1988 | Seiderman | 604/20 |
| 4,820,263 | 4/1989 | Spevak et al. | 604/20 |
| 4,927,408 | 5/1990 | Haak et al. | 604/20 |
| 5,084,006 | 1/1992 | Lew et al. | 604/20 |

FOREIGN PATENT DOCUMENTS 0410009 5/1934 United Kingdom .

Primary Examiner—Lee S. Cohen
Assistant Examiner—K. M. Pfaffle
Attorney, Agent, or Firm—D. Byron Miller; Edward L. Mandell; Steven F. Stone

[57] ABSTRACT

An iontophoretic agent delivery device having donor and counter electrodes comprised of either metal or a hydrophobic polymer loaded with a conductive filler is provided. The agent reservoir in the donor electrode assembly contains about 10 to 60 wt % hydrophobic polymer, about 10 to 60 wt % hydrophilic polymer, and up to 50% agent. Similarly, the electrolyte reservoir contains about 10 to 60 wt % hydrophobic polymer, about 10 to 60 wt % hydrophilic polymer, and up to 50% electrolyte. The agent reservoir, the electrolyte reservoir and the electrodes are preferably in the form of films which are laminated to one another. The hydrophobic polymer component in the agent/electrolyte reservoir prevents the reservoir from delaminating from the metal/hydrophobic polymer based electrode, even after hydration of the reservoirs.

32 Claims, 2 Drawing Sheets

IONTOPHORETIC DELIVERY DEVICE

This application is a continuation of Ser. No. 07/502,608, filed Mar. 30, 1990, now U.S. Pat. No. 5,984,006, and benefit of the filing date of said earlier filed application is claimed under 35 U.S.C. §120.

TECHNICAL FIELD

This invention relates to a device for delivering an agent transdermally or transmucosally by iontophoresis. More particularly, this invention relates to an electrically powered iontophoretic delivery device having an agent reservoir at least partially composed of a hydrophobic polymer.

BACKGROUND ART

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is the transdermal flux of a liquid solvent (e.g., the liquid solvent containing the uncharged drug or agent) which is induced by the presence of an electric field imposed across the skin by the donor electrode.

Furthermore, existing iontophoresis devices generally require a reservoir or source of the beneficial agent (which is preferably an ionized or ionizable agent or a precursor of such agent) to be iontophoretically delivered or introduced into the body. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,383,529 and Ariura et al. U.S. Pat. No. 4,474,570. Such drug reservoirs are electrically connected to the anode or the cathode of an iontophoresis device to provide a fixed or renewable source of one or more desired agents.

More recently, iontophoretic delivery devices have been developed in which the donor and counter electrode assemblies have a "multi-laminate" construction. In these devices, the donor and counter electrode assemblies are each formed by multiple layers of (usually) polymeric matrices. For example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. In addition, Ariura et al, U.S. Pat. No. 4,474,570 discloses a device wherein the electrode assemblies include a conductive resin film electrode layer, a hydrophilic gel reservoir layer, and aluminum foil conductor layer and an insulating backing layer.

The drug and electrolyte reservoir layers of iontophoretic delivery devices have been formed of hydrophilic polymers. See for example, Ariura et al, U.S. Pat. No. 4,474,570; Webster U.S. Pat. No. 4,383,529 and Sasaki U.S. Pat. No. 4,764,164. There are several reasons for using hydrophilic polymers. First, water is a the preferred solvent for ionizing many drug salts. Secondly, hydrophilic polymer components (i.e., the drug reservoir in the donor electrode and the electrolyte reservoir in the counter electrode) can be hydrated in situ (i.e., while attached to the body) by absorbing water from the skin (i.e., through transepidermal water loss or sweat) or from a mucosal membrane (e.g., by absorbing saliva in the case of oral mucosal membranes). Once hydrated, the device begins to deliver ionized agent to the body. This enables the drug reservoir to be manufactured in a dry state, giving the device a longer shelf life.

Hydrogels have been particularly favored for use as the drug reservoir matrix and electrolyte reservoir matrix in iontophoretic delivery devices, in part due to their high equilibrium water content and their ability to quickly absorb water. In addition, hydrogels tend to have good biocompatibility with the skin and with mucosal membranes. In spite of these advantages however, hydrogels and other hydrophilic polymer components are difficult to laminate to other components of the delivery system. For example, when utilizing a drug reservoir matrix or an electrolyte reservoir matrix composed of a hydrophilic polymer, the matrix begins to swell as it absorbs water from the skin. In the case of hydrogels, the swelling is quite pronounced. Typically, the drug or electrolyte reservoir is in either direct contact, or contact through a thin layer of an electrically conductive adhesive, with an electrode. Typically, the electrode is composed of metal (e.g., a metal foil or a thin layer of metal deposited on a backing layer) or a hydrophobic polymer containing a conductive filler (e.g., a hydrophobic polymer loaded with carbon fibers and/or metal particles). The electrodes (i.e., either metal electrodes or hydrophobic polymers containing a conductive filler), on the other hand, do not absorb water and do not swell. The different swelling properties of the hydrophilic reservoirs and the electrodes results in shearing along their contact surfaces. In severe cases, the shearing action can result in the complete loss of electrical contact between the electrode and the reservoir resulting in an inoperable device.

DISCLOSURE OF THE INVENTION

It is an object of this invention to provide improved drug reservoir and electrolyte reservoir matrices for an iontophoretic delivery device.

It is another object of this invention to provide an improved iontophoretic delivery device which avoids the delamination problems of the prior art iontophoretic drug delivery devices.

These and other objects are met by an electrically powered iontophoretic agent delivery device which includes a donor electrode assembly, a counter electrode assembly and a source of electrical power adapted to be electrically connected to the donor and counter electrode assembies. The donor electrode assembly includes an agent reservoir containing the agent to be delivered. The agent reservoir is adapted to be placed in agent transmitting relation with a body surface, such as intact skin or a mucosal membrane. The donor electrode assembly also includes a donor electrode adapted to be electrically connected to the source of electrical power. The donor electrode has a surface which is in contact with the agent reservoir. The agent reservoir is comprised of about 10 to 60 wt % of a hydrophilic polymer, about 10 to 60 wt % of a hydrophobic polymer, and up to about 50 wt % of the agent. Such an agent reservoir can be secured, by laminating, to either a metal foil electrode or a hydrophobic polymer based electrode, and has a greatly reduced tendency to delaminate from the electrode even after the agent reservoir becomes hydrated.

In a preferred embodiment, the counter electrode assembly of the delivery device includes a counter electrode adapted to be electrically connected to the source of electrical power and an electrolyte reservoir adapted to be placed in electrolyte transmitting relation with the body. The counter electrode has a surface which is in contact with the electrolyte reservoir. The electrolyte reservoir is also comprised of about 10 to 60 wt % of a hydrophilic polymer, about 10 to 60 wt % of a hydrophobic polymer, and up to about 60 wt % of the electrolyte. Such an electrolyte reservoir can be secured, by laminating, to either a metal foil electrode or a hydrophobic polymer based electrode, and has a greatly reduced tendency to delaminate from the electrode even after the electrolyte reservoir becomes hydrated.

MODES FOR CARRYING OUT THE INVENTION

Figure 1:
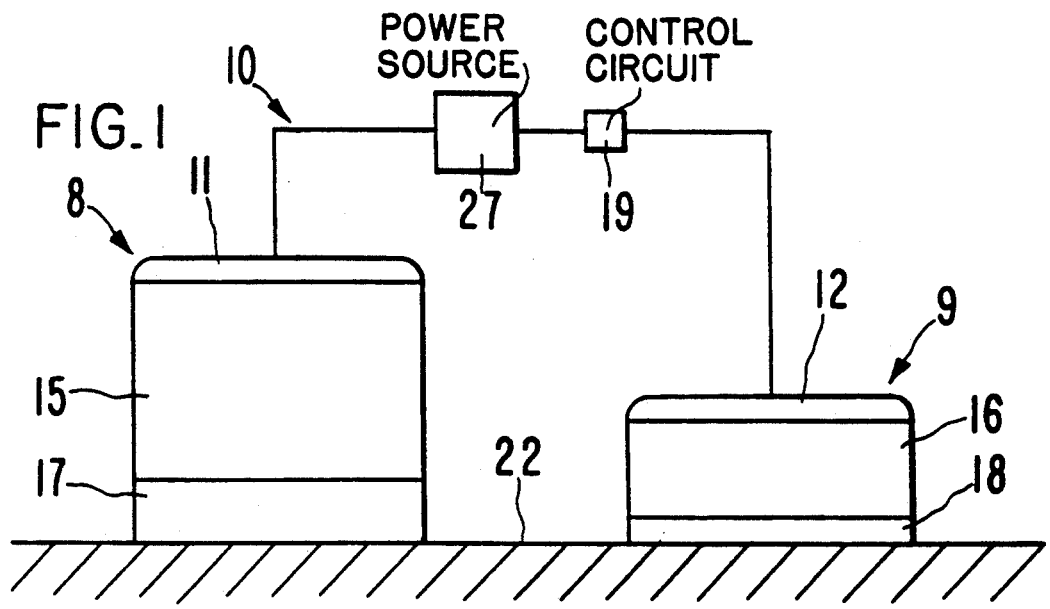
FIG. 1 is a schematic view of an iontophoretic drug delivery device according to the present invention.

FIG. 1 is a schematic view of an iontophoretic delivery device 10 for delivering a beneficial agent through a body surface 22. Body surface 22 is typically intact skin or a mucosal membrane. Iontophoretic delivery device 10 includes a donor electrode assembly 8 and a counter electrode assembly 9. Electrode assemblies 8 and 9 are connected in series with an electrical power source 27, which is typically one or more low voltage batteries, and an optional control circuit 19 which is described in more detail hereinafter. When the device 10 is in storage, no current flows because the device does not form a closed circuit. When the device 10 is placed on the skin or mucosal membrane of a patient and the electrode assemblies 8 and 9 are hydrated, the circuit between the electrodes is closed and the power source begins to deliver current through the device and through the body of the patient. The donor and counter electrode assemblies 8 and 9 normally include a strippable release liner, not shown, which is removed prior to application of electrode assemblies 8 and 9 to body surface 22.

The donor electrode assembly 8 includes a donor electrode 11 and an agent reservoir 15. The agent reservoir 15 contains the beneficial agent to be iontophoretically delivered by device 10. The donor electrode assembly 8 is adhered to the body surface 22 by means of an ion-conducting adhesive layer 17.

Device 10 includes a counter electrode assembly 9 which is placed on the body surface 22 at a location spaced apart from electrode assembly 8. Counter electrode assembly 9 includes a counter electrode 12 and an electrolyte reservoir 16. Counter electrode assembly 9 is adhered to the body surface 22 by means of an ion-conducting adhesive layer 18. As an alternative to the ion-conducting adhesive layers 17 and 18 shown in FIGS. 1 and 2, the iontophoretic delivery devices 10 and 20 may be adhered to the skin using an adhesive overlay. Any of the conventional adhesive overlays used to secure passive transdermal delivery devices to the skin may be used.

Electrodes 11 and 12 are electrically conductive and may be formed of a metal, e.g., a metal foil or metal deposited or painted on a suitable backing. Examples of suitable metals include silver, zinc, silver/silver chloride, aluminum, platinum, stainless steel, gold and titanium. Alternatively, the electrodes 11 and 12 may be formed of a hydrophobic polymer matrix containing a conductive filler such as a metal powder, powdered graphite, carbon fibers or other known electrically conductive filler material. The hydrophobic polymer based electrodes may be made by mixing the conductive filler in the hydrophobic polymer matrix. For example, zinc powder, silver powder, silver/silver chloride powder, powdered carbon, carbon fibers and mixtures thereof can be mixed in a hydrophobic polymer (e.g., an ethylene vinyl acetate copolymer) matrix, with the preferred amount of conductive filler being within the range of about 30 to 90 vol % and the remainder being the hydrophobic polymer matrix.

Electrodes 11 and 12 are electrically connected to power source 27 using well known means, e.g., printed flexible circuits, metal foils, wires or by direct contact. As an alternative to a battery as the power source 27, device 10 can be powered by a galvanic couple formed by the donor electrode 11 and counter electrode 12 being composed of dissimilar electrochemical couples and being placed in electrical contact with one other. Typical galvanic couple materials for delivering a cationic agent include a zinc donor electrode 11 and a silver/silver chloride counter electrode 12. A Zn-Ag/AgCl galvanic couple provides an electrical potential of about 1 volt.

The electrolyte reservoir 16 contains a suitable pharmacologically acceptable salt. Suitable salts include sodium chloride, alkali metal salts, alkaline earth metal salts such as chlorides, sulfates, nitrates, carbonates, phosphates, and organic salts such as ascorbates, citrates, acetates and mixtures thereof. Reservoir 16 may also contain a buffering agent. Sodium chloride is a suitable electrolyte when the counter electrode 12 is the cathode and is composed of silver/silver chloride, optionally with a sodium phosphate buffer.

Figure 2:
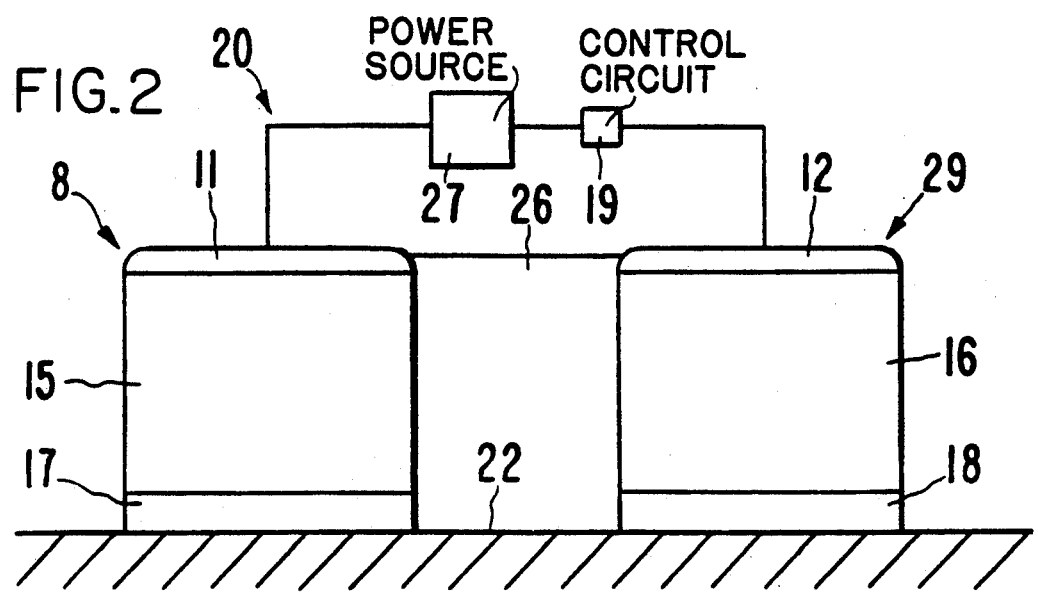
FIG. 2 is a schematic view of another embodiment of an iontophoretic delivery device according to the present invention.

FIG. 2 illustrates another iontophoretic delivery device designated by the numeral 20. Like device 10, device 20 also contains an electrical power source 27 (e.g., a battery) and an optional control circuit 19. However, in device 20 the donor electrode assembly 8 and the counter electrode assembly 9 are physically attached to insulator 26 and form a single self-contained unit. Insulator 26 prevents the electrode assemblies 8 and 9 from short circuiting the body by preventing electrical and/or ion transport between the electrode assemblies 8 and 9. Insulator 26 is preferably formed of a hydrophobic non-conducting polymeric material which is impermeable to both the passage of ions and water. Preferred insulating materials are nonporous ethylene vinyl acetate and closed cell foamed plastics.

The agent reservoir and the electrolyte reservoir according to the present invention are each comprised of about 10 to 60 wt % of a hydrophilic polymer and about 10 to 60 wt % of a hydrophobic polymer; preferably about 20 to 40 wt % of a hydrophilic polymer and about 30 to 50 wt % of a hydrophobic polymer; and most preferably about 25 wt % of a hydrophilic polymer and about 40 wt % of a hydrophobic polymer. The agent reservoir matrix contains up to about 60 wt % of the agent, preferably about 25 to 50 wt % of the agent and most preferably about 35 wt % of the agent. The electrolyte reservoir matrix contains up to about 60 wt % of the electrolyte, preferably about 25 to 50 wt % of the electrolyte and most preferably about 35 wt % of the electrolyte.

As used herein, a hydrophilic polymer is a polymer having an equilibrium water content of at least 20 wt %, preferably at least about 30 wt % and most preferably at least about 40 wt % after prolonged exposure to an atmosphere having a relative humidity of over about 90%. Also as used herein, a hydrophobic polymer is any polymer having an equilibrium water content of less than 20 wt %, preferably less than about 15 wt % and most preferably less than about 10 wt % after prolonged exposure to an atmosphere having a relative humidity of over about 90%.

A suitable minimum amount of hydrophilic polymer is that which provides an interconnecting network of the hydrophilic polymer pathways throughout the reservoir, generally at least about 10 wt % hydrophilic polymer. On the other hand, a suitable minimum amount of hydrophobic polymer is that which provides sufficient structure to bond to another hydrophobic surface. Preferably, the hydrophobic polymer is heat fusible and can be heat fused to another polymeric surface such as a polymer based electrode or a membrane. Alternatively, if the electrode is composed of a metal, such as a metal plate, a metal foil or a metalized surface on a suitable backing material, the hydrophobic polymer preferably contains a resinous tackifying agent.

Suitable hydrophobic polymers for use in the matrix of reservoirs 15 and 16 include, without limitation, polyethylene, polypropylene, polyisoprenes and polyalkenes, rubbers, copolymers such as Kraton ®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, and itaconic acid, N-branched alkyl maleamic acids wherein the alkyl group has 10-24 carbon atoms, glycol diacrylates, and blends thereof. Most of the above listed hydrophobic polymers are heat fusible. Of these, ethylene vinyl acetate copolymers are preferred.

In cases where the electrode is a metal foil or a metalized polymeric film, it may be necessary to add a tackifying resin to the hydrophobic polymer component in order to enhance its adhesiveness. Suitable hydrophobic polymers which can be rendered more adhesive by the addition of tackifying resins include, without limitation, cellulose acetate, cellulose acetate butyrate, ethylcellulose, poly(styrene-butadiene) and poly(styrene-isoprene-styrene) block copolymers, ethylene vinyl acetate copolymers such as those which are described in U.S. Pat. No. 4,144,317, plasticized or unplasticized polyvinylchloride, natural or synthetic rubbers, $C_2$–$C_4$ polyolefins such as polyethylene, polyisoprene, polyisobutylene and polybutadiene. Examples of suitable tackifying resins include, without limitation, fully hydrogenated aromatic hydrocarbon resins, hydrogenated esters and low molecular weight grades of polyisobutylene. Particularly suitable are tackifiers sold under the trademarks Staybelite Ester ® #5 and #10, Regal-Rez ® and Piccotac ®, by Hercules, Inc. of Wilmington, Del.

Suitable hydrophilic polymers for use in the matrix of reservoirs 15 and 16 include polyvinylpyrrolidones, polyvinyl alcohol, polyethylene oxides such as Polyox ® manufactured by Union Carbide Corp., Carbopol ® manufactured by BF Goodrich of Akron, Ohio; blends of polyoxyethylene or polyethylene glycols with polyacrylic acid such as Polyox ® blended with Carbopol ®, polyacrylamide, Klucel ®, cross-linked dextran such as Sephadex (Pharmacia Fine Chemicals, AB, Uppsala, Sweden), Water Lock ® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl methacrylate (National Patent Development Corp.), natural gums, chitosan, pectin, starch, guar gum, locust bean gum, and the like, along with blends thereof. Of these, polyvinylpyrrolidones are preferred.

Blending of the drug or electrolyte with the hydrophobic and hydrophilic polymer components is done mechanically, either in solution or by milling, extrusion or hot melt mixing, for example. The resulting reservoir layers may then be prepared by solvent casting, extrusion or by melt processing, for example.

In addition to the drug and electrolyte, the reservoirs 15 and 16 may also contain other conventional materials such as dyes, pigments, inert fillers, and other excipients.

The two phase reservoir matrix according to this invention has hydrophilic pathways in order to allow agent and/or electrolyte (e.g., agent or electrolyte ions) to pass through the reservoir under the influence of an electric field, i.e., the reservoir presents minimal mass transport resistance. The reservoir also has good hydration kinetics so that the time it takes to absorb water (e.g., from the body) and begin passing current, is acceptable. A suitable time to reach steady state moisture content is less than about 5 hours, preferably less than 1 hour, most preferably less than 10 minutes. Further, the reservoir layer provides for uniform current distribution so as to avoid highly localized current densities which could result in tissue damage.

The reservoir matrix of the present invention exhibits excellent ionic conductivity so it is not rate limiting and does not require significant voltage during system operation, i.e., the reservoir presents minimal electrical resistance. By incorporating the hydrophilic polymer phase, the reservoir of this invention has been shown to exhibit an area resistance of less than about 10 kohm-cm$^2$, preferably less than about 5 kohm-cm$^2$, most preferably less than about 1 kohm-cm$^2$ for reservoirs having a thickness of about 3 mils.

A control circuit 19 is optionally provided. Control circuit 19 may take the form of an on-off switch for "on-demand" drug delivery (e.g., patient controlled delivery of an analgesic for pain relief), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of current from device 10 since a constant current level ensures that the drug or agent is delivered through the skin at a constant rate. The current level can be controlled by a variety of known means, for example, a resistor or a simple circuit that employs a resistor and a field effect transistor. Control circuit 19 may also include an integrated circuit which could be designed to control the dosage of beneficial agent, or even to respond to sensor signals in order to regulate the dosage to maintain a predetermined dosage regimen. A relatively simple circuit can control the current as a function of time, and if desired, generate complex current waveforms such as pulses or sinusoidal waves. In addition, the control circuit 19 may employ a bio-feedback system which monitors a biosignal, provides an assessment of the therapy, and adjusts the drug delivery accordingly. A typical example is the monitoring of the blood sugar level for controlled administration of insulin to a diabetic patient.

Alternatively, both the donor electrode assembly 8 and the counter electrode assembly 9 may be used to iontophoretically deliver different beneficial agents through body surface 22. For example, positive agent ions can be delivered through body surface 22 from the anode electrode assembly, while negative agent ions can be delivered from the cathode electrode assembly. Alternatively, neutral drugs can be introduced from either electrode assembly by electroosmosis.

As an alternative to the side-by-side alignment of the donor electrode assembly 8, the insulator 26 and the counter electrode assembly 9 shown in FIG. 2, the electrode assemblies can be concentrically aligned with the counter electrode assembly positioned centrally and surrounded by the insulator 26 and the donor electrode assembly. The electrode assemblies can, if desired, be reversed with the counter electrode assembly surrounding the centrally positioned donor electrode assembly. The concentric alignment of the electrode assemblies can be circular, elliptical, rectangular or any of a variety of geometric configurations.

The combined skin-contacting areas of electrode assemblies 8 and 9 can vary from less than 1 cm$^2$ to greater than 200 cm$^2$. The average device 10 however, will have electrode assemblies with a combined skin-contacting area within the range of about 5-50 cm$^2$.

This invention has utility in connection with the delivery of drugs within the class which can be delivered through body surfaces. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers. It is most preferable to use a water soluble salt of the drug or agent to be delivered although non-ionized agents can be delivered from delivery devices 10 and 20 by the process of electroosmosis.

The invention is also useful in the controlled delivery of peptides, polypeptides, proteins and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, αANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

Having thus generally described our invention, the following examples will illustrate preferred embodiments thereof.

EXAMPLE I

A drug reservoir for an iontophoretic delivery device was made by mixing the following materials: 25 parts by weight of hydrophilic polyvinylpyrrolidone (Polyplasdone XL ®-10 sold by GAF Corp., Wayne, N.J.); 35 parts by weight of an ionizable model drug salt (positively charged drug ions and negatively charged counter ions); and 40 parts by weight of a hydrophobic ethylene vinyl acetate copolymer having a vinyl acetate content of 28% (EVA 28). The materials were mixed in a 50 cm$^3$ Brabender mixer (Model 0040/SB sold by C. W. Brabender Instruments, Inc., South Hackensack, NJ). The mixer bowl was heated to a temperature of 70° C. and the blade speed was 40 rpm. The materials were mixed for about 20 minutes.

The mixture was then melt-pressed in a hydraulic press (Pasadena Hydraulics, Inc., El Monte, Calif., Model No. PM-220) at a pressure of 30,000 psig and a temperature of 85° C. The film had a thickness of about 12 mils. The film was then laminated onto a hydrophobic polymer based electrode. The electrode was composed of an ethylene vinyl acetate copolymer having a vinyl acetate content of 9% (EVA 9) loaded with an electrochemically oxidizable material and carbon fibers. The film and the polymer based electrode were then placed over a heated hot plate (temperature of about 80° to 100° C.) and laminated together by manually applying pressure with a roller. The laminated electrode reservoir assembly was then exposed to a 95% relative humidity atmosphere in a glass desiccator chamber containing a saturated solution of Na$_2$HPO$_4$.7H$_2$O at room temperature and allowed to hydrate overnight. Good intimate contact was maintained between the EVA 9 based electrode and the drug reservoir both during and after hydration.

EXAMPLE II

The reservoir matrix material of Example I was used in both the drug reservoir and the electrolyte reservoir of an iontophoretic drug delivery device. Metoclopramide HCL in the amount of 35 wt %, was mixed into the drug reservoir matrix material and was extruded in the form of a sheet having a thickness of 6 mils. The donor electrode had the same composition as the EVA 9 based electrode described in Example I. The donor electrode was secured to the drug reservoir by laminating the electrode to the reservoir using heat and pressure.

Figure 3:
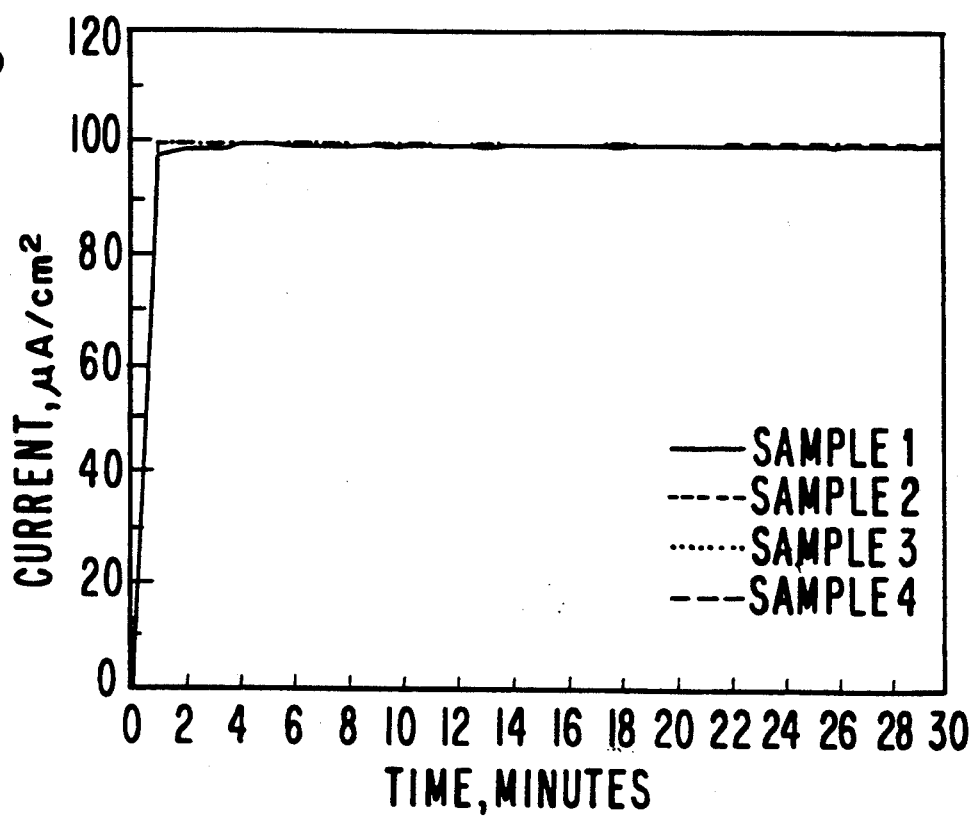
FIG. 3 is a graph of the current density over time for an electrode assembly described in Example II.

Four samples of the donor electrode/drug reservoir assembly were each cut from the laminate and placed in a permeation cell. The drug reservoir side of the laminate was placed in contact with a compartment containing Dulbecco's phosphate buffered saline solution (pH 7). An Ag/AgCl electrode was placed in the Dulbecco's solution. A power source delivering 100 μA/cm$^2$ of direct current was connected between the polymer electrode of the laminate and the Ag/AgCl electrode. The current passed through each of the laminates was measured as a function of time and the data is shown in FIG. 3. For the four samples tested, the drug reservoirs became sufficiently hydrated to pass substantially all of the current after only about 1 to 2 minutes. FIG. 3 shows that the drug reservoir matrix material of the present invention may be quickly hydrated to begin delivering drugs (as shown by the ionic conduction of the model drug salt through the reservoir) within a matter of minutes.

Figure 4:
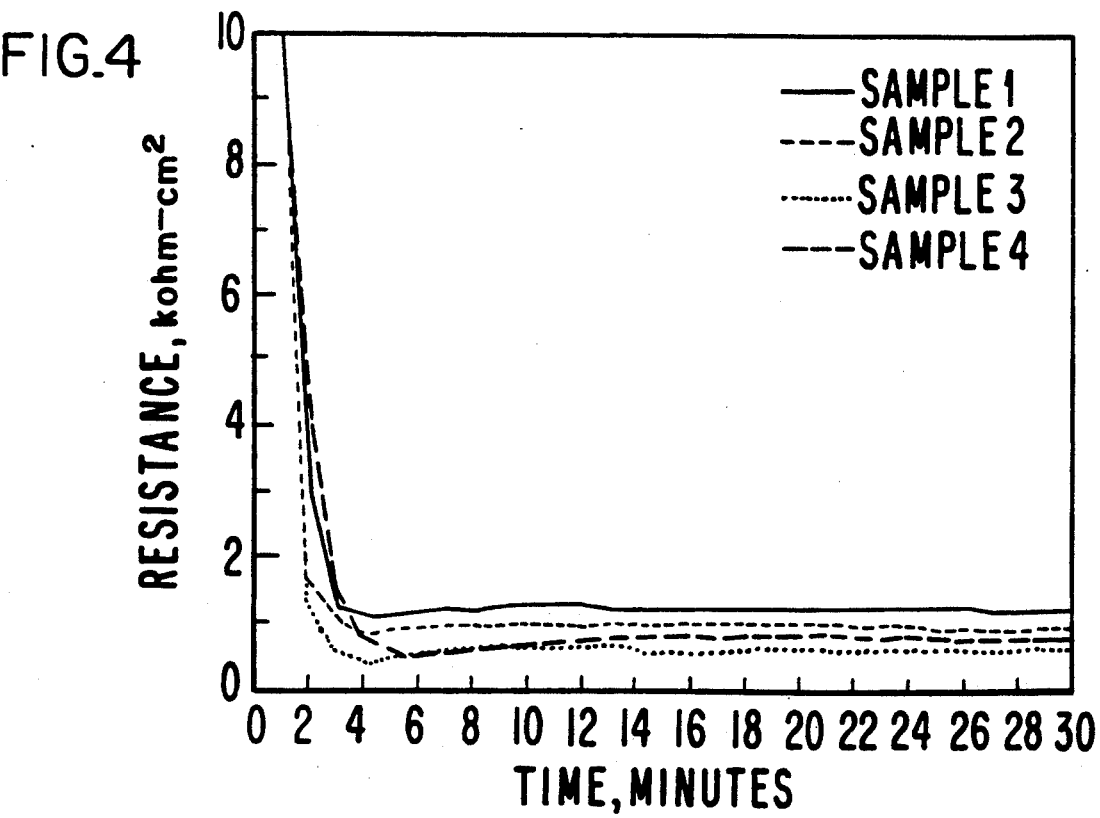
FIG. 4 is a graph of the electrical resistance over time for an electrode assembly described in Example II.

The resistance of the laminate was also monitored over time by measuring the voltage drop across a standard 10 kohm resistor using a voltmeter and then calculating the resistance using Ohm's law (R=I/V). The results are shown in FIG. 4. For all four samples tested, the laminates exhibited a resistance of only about 1 kohm . cm$^2$ after several minutes exposure to the Dulbecco's solution.

A counter electrode assembly including a counter electrode and an electrolyte reservoir was also constructed. The counter electrode was composed of EVA 9 loaded with an electrochemically reducible material and carbon fibers. Sodium Chloride, in the amount of 35 wt %, was mixed into the electrolyte reservoir matrix material and was extruded in the form of a sheet having a thickness of 6 mils. The counter electrode was secured to the electrolyte reservoir by laminating using heat and pressure.

The above-described donor and counter electrode assemblies can be electrically connected to a low voltage battery and such a device is effective to delivery metoclopramide transdermally.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An electrically powered iontophoretic agent delivery device including a donor electrode assembly, a counter electrode assembly and a source of electrical power electrically connected to the donor electrode assembly and the counter electrode assembly, the donor electrode assembly comprising:
   a) an agent reservoir containing an agent, the agent reservoir adapted to be placed in agent transmitting relation with a body surface; and
   b) a donor electrode electrically connected to the source of electrical power, the donor electrode also being in electrical contact with the agent reservoir;
   wherein the agent reservoir is comprised of about 10 to 60 wt % of a polyvinylpyrrolidone, about 10 to 60 wt % of a solid heat fusible polyisobutylene and up to about 60 wt % of the agent.

2. The device of claim 1, wherein the donor electrode is comprised of a metal.

3. The device of claim 2, wherein the metal is selected from the group consisting of silver and zinc.

4. The device of claim 1, wherein the donor electrode comprises a hydrophobic polymer matrix containing a conductive filler.

5. The device of claim 4, wherein the conductive filler comprises metal particles.

6. The device of claim 4, wherein the conductive filler comprises carbon fibers.

7. The device of claim 4, wherein the agent reservoir and the donor electrode are each in the form of a film.

8. The device of claim 7, wherein the donor electrode and the agent reservoir are laminated to one another.

9. The device of claim 7, wherein the films are adhered to one other with an ionically conductive adhesive.

10. The device of claim 1, wherein the counter electrode assembly includes a counter electrode electrically connected to the source of electrical power and an electrolyte reservoir adapted to be placed in electrolyte transmitting relation with the body surface, the counter electrode also being in electrical contact with the electrolyte reservoir;
   wherein the electrolyte reservoir is comprised of about 10 to 60 wt % of a polyvinylpyrrolidone, about 10 to 60 wt % of a solid heat fusible polyisobutylene and up to about 50 wt % of the electrolyte.

11. The device of claim 10, wherein the counter electrode is comprised of a metal.

12. The device of claim 11, wherein the metal is selected from the group consisting of silver and zinc.

13. The device of claim 10, wherein the counter electrode is comprised of a hydrophobic polymer containing a conductive filler.

14. The device of claim 13, wherein the conductive filler comprises metal particles.

15. The device of claim 13, wherein the conductive filler comprises carbon fibers.

16. The device of claim 13, wherein the counter electrode and the electrolyte reservoir are each in the form of a film.

17. The device of claim 16, wherein the counter electrode and the electrolyte reservoir are laminated to one another.

18. The device of claim 16, wherein the films are adhered to one another with an ionically conductive adhesive.

19. The device of claim 10, wherein the electrolyte reservoir also comprises a tackifying resin.

20. The device of claim 19, wherein the tackifying resin comprises a low molecular weight polyisobutylene.

21. The device of claim 10, wherein the electrolyte reservoir comprises about 20 to 40 wt % polyvinylpyrrolidone.

22. The device of claim 10, wherein the electrolyte reservoir comprises about 30 to 50 wt % polyisobutylene.

23. The device of claim 10, wherein the electrolyte reservoir comprises about 25 to 50 wt % of the electrolyte.

24. The device of claim 10, wherein the electrolyte reservoir also contains a polyethylene glycol.

25. The device of claim 10, wherein the polyvinylpyrrolidone is crosslinked.

26. The device of claim 1, wherein the agent reservoir also comprises a tackifying resin.

27. The device of claim 26, wherein the tackifying resin comprises a low molecular weight polyisobutylene.

28. The device of claim 1, wherein the agent reservoir comprises about 20 to 40 wt % polyvinylpyrrolidone.

29. The device of claim 1, wherein the agent reservoir comprises about 30 to 50 wt % polyisobutylene.

30. The device of claim 1, wherein the agent reservoir comprises about 25 to 50 wt % of the agent.

31. The device of claim 1, wherein the agent reservoir also contains a polyethylene glycol.

32. The device of claim 1, wherein the polyvinylpyrrolidone is crosslinked.

* * * * *